(12) United States Patent
Kim et al.

(10) Patent No.: US 8,734,831 B2
(45) Date of Patent: May 27, 2014

(54) METHOD FOR MANUFACTURING A POROUS CERAMIC SCAFFOLD HAVING AN ORGANIC/INORGANIC HYBRID COATING LAYER CONTAINING A BIOACTIVE FACTOR

(75) Inventors: Hyoun-Ee Kim, Seoul (KR); Shin-Hee Jun, Seoul (KR); Eun-Jung Lee, Gyeonggi-do (KR)

(73) Assignee: SNU R&DB Foundation, Seoul (KR)

( * ) Notice: Subject to any disclaimer, the term of this patent is extended or adjusted under 35 U.S.C. 154(b) by 168 days.

(21) Appl. No.: 13/088,304

(22) Filed: Apr. 15, 2011

(65) Prior Publication Data

US 2011/0256203 A1 Oct. 20, 2011

Related U.S. Application Data

(60) Provisional application No. 61/325,118, filed on Apr. 16, 2010.

(51) Int. Cl.
| | | |
|---|---|---|
| *A61K 33/00* | (2006.01) | |
| *A61K 33/06* | (2006.01) | |
| *A61K 33/08* | (2006.01) | |
| *A61K 33/42* | (2006.01) | |
| *A61F 2/00* | (2006.01) | |
| *A61F 2/28* | (2006.01) | |
| *A61L 24/00* | (2006.01) | |
| *A61L 24/02* | (2006.01) | |

(52) U.S. Cl.
USPC ........... 424/423; 424/422; 424/426; 424/602; 424/724; 514/1.1; 514/3.1; 514/5.9; 514/39; 514/40; 514/152; 514/192; 514/200; 514/422; 514/449

(58) Field of Classification Search
None
See application file for complete search history.

(56) References Cited

U.S. PATENT DOCUMENTS 5,674,468 A * 10/1997 Klaveness et al. ............. 424/9.3
2007/0292525 A1* 12/2007 Barbe et al. ................... 424/501

FOREIGN PATENT DOCUMENTS

KR 1020050075663 A 7/2005

OTHER PUBLICATIONS

Soundrapandian et al. (AAPS PharmSciTech 2009, 10(4), 1158-1171).*
Derwent-Acc-No. 2009-J21460 (abstracting KR 2009044858).*
Lee et al. (Biomaterials 2009, 30, 743-750; available online Nov. 22, 2008).*
Lee, Eun-Jung et al.; "Silica xerogel-chitosan nano-hybrids for use as drug eluting bone replacement"; J Mater Sci: Mater Med; 2010; 21; pp. 207-214.

* cited by examiner

*Primary Examiner* — Ernst Arnold
(74) *Attorney, Agent, or Firm* — Rabin & Berdo, P.C.

(57) ABSTRACT

A method for manufacturing a porous ceramic scaffold having an organic/inorganic hybrid coating layer containing a bioactive factor includes (a) forming a porous ceramic scaffold; (b) mixing a silica xerogel and a physiologically active organic substance in a volumetric ratio ranging from 30:70 to 90:10 and treating by a sol gel method to prepare an organic/inorganic hybrid composite solution; (c) adding a bioactive factor to the organic/inorganic hybrid composite solution and agitating until gelation occurs; and (d) coating the porous ceramic scaffold with the organic/inorganic composite containing the bioactive factor added thereto. In accordance with the method, the porous ceramic scaffold may be uniformly coated with the organic/inorganic hybrid composite while maintaining an open pore structure, and stably discharge the bioactive factor over a long period of time.

12 Claims, 4 Drawing Sheets

METHOD FOR MANUFACTURING A POROUS CERAMIC SCAFFOLD HAVING AN ORGANIC/INORGANIC HYBRID COATING LAYER CONTAINING A BIOACTIVE FACTOR

BACKGROUND OF THE INVENTION

1. Field of the Invention

The present invention relates to a porous ceramic scaffold having an organic/inorganic hybrid composite coating layer that includes a bioactive factor, as well as a method for production of the same. More particularly, the present invention relates to a porous ceramic scaffold for biomedical applications, uniformly coated with a hybrid composite that contains a bioactive factor and is formed of a high bioactivity silica xerogel and a physiologically active organic substance, as well as a method for manufacturing the same.

2. Description of the Related Art

As general medical operations to recover bone defects, autogenous and/or allogeneic bone graft methods have been employed since early times. However, autogenous bones are not provided in a sufficient amount to recover overall bone defects and have a problem of requiring secondary operation at a donor site. Allogeneic bones have disadvantages of causing infection or infectious diseases. Therefore, extensive research and development into bone graft materials using artificial materials with biostability but without worry about infections have recently been conducted.

As such materials, bio-inert (or bio-inactive) ceramic materials such as alumina, zirconia, etc., or bio-active ceramic materials such as hydroxyapatite, calcium phosphate based ceramics (that is, tricalcium phosphate (TCP), biphasic calcium phosphate (BCP)), etc., are broadly employed.

Specifically, in order to fabricate a scaffold similar to biological tissues, attempts to fabricate a scaffold having a pore structure have been implemented. It is known that such a pore structure enables tissue cells to be suitably adhered to a scaffold and may induce and accelerate regeneration of tissues. The foregoing method for fabrication of a porous structural scaffold may include, for example: a salt-leaching process that includes mixing ceramic molecules with insoluble particles such as salt in a solvent and casting the mixture, followed by removal of the solvent and particles to thereby form pores; a sponge-method that includes using a sponge material such as polyurethane foam, as a basic framework, injecting a ceramic slurry thereto to coat the framework, and removing the sponge through heat treatment, to thereby form a porous body; a freeze drying method that includes preparing a ceramic slurry in water and freeze-drying the slurry to form a porous body, or the like. Meanwhile, Korean Patent No. 879127, entitled "Method for controlling pores of porous material through freeze-casting and porous material manufactured by the same," invented by the present inventors, discloses a process for manufacturing a porous ceramic scaffold through freeze-drying using camphene. According to this technique, porosity, pore size, pore arrangement, or the like may be easily controlled while maintaining an open pore structure of the porous material.

In order to induce rapid tissue regeneration in vivo, in addition to the attempts for improvement of structural materials described above, attempts to deliver a variety of body vitality factors (often referred to as 'bioactive factors') capable of directly inducing tissue regeneration as well as the material have recently been conducted. However, such a ceramic material principally needs heat treatment at a high temperature, thus entailing a limitation in delivering bioactive factors. There was an attempt to spray a solution containing bioactive factors over a porous scaffold to thereby deliver the bioactive factors adhered to a surface of the scaffold. However, such method has a difficulty in stably delivering the bioactive factors for a long time. Further, although studies into an improved porous scaffold having a coating layer formed of a biopolymer, in which bioactive factors are loaded, have currently been conducted, this method has also a limitation in controlling loading capacity and discharge capacity of the bioactive factors.

SUMMARY OF THE INVENTION

Therefore, the present invention has been made in view of the above problems, and it is an object of the present invention to provide a porous ceramic scaffold for biomedical applications, which is fabricated at room temperature, exhibits superior biocompatibility, and has an organic/inorganic hybrid coating layer containing a bioactive factor wherein the coating layer is formed by applying an organic/inorganic hybrid composite, that enables a variety of bioactive factors to be loaded therein and easy control of loading capacity and discharge capacity of the bioactive factors, to a pore structure of a porous material, as well as a method for manufacturing the same.

In accordance with the present invention, the above and other objects can be accomplished by the provision of a method for manufacturing a porous ceramic scaffold, which has an organic/inorganic hybrid coating layer containing a bioactive factor, including: (a) forming a porous ceramic scaffold; (b) mixing silica xerogel and a physiologically active organic substance to form an organic/inorganic hybrid composite; (c) adding a bioactive factor to the organic/inorganic hybrid composite; and (d) coating a pore structure of the porous ceramic scaffold with the organic/inorganic hybrid composite containing the bioactive factor.

Ceramic materials used for the foregoing porous ceramic scaffold may include biostable ceramics, for example, calcium phosphate materials such as hydroxyapatite, tricalcium phosphate (TCP), biphasic calcium phosphate (BCP), etc., alumina, zirconia, and so forth.

Step (b) includes preparing an organic/inorganic hybrid solution by a sol-gel method and using the silica xerogel and the physiologically active organic substance, wherein a constituent ratio of the silica xerogel to the physiologically active organic substance may be 30~90:70~10 (by volume).

Step (c) includes supporting (or loading) the bioactive factor in the organic/inorganic hybrid composite solution under agitation, and agitating the hybrid composite solution (containing the bioactive factor) until a gel is formed.

Step (d) may include: (d1) loading the ceramic scaffold with the organic/inorganic hybrid composite solution containing the bioactive factor; (d2) freezing the solution loaded ceramic scaffold at a predetermined temperature; and (d3) freeze-drying the scaffold to remove the solvent while maintaining a vacuum condition.

In Step (a), the porous ceramic scaffold may be loaded with the organic/inorganic hybrid composite solution containing the bioactive factor under vacuum. Meanwhile, the processes of Steps (b) to (d) may be conducted at room temperature.

According to the present invention, biocompatibility and bioactivity of a porous ceramic scaffold may be favorably improved by coating a pore structure of the porous ceramic scaffold with an organic/inorganic hybrid composite. Also, coating of a pore structure with an organic/inorganic hybrid composite may increase a surface area of a ceramic scaffold and enable a bioactive factor to be easily added thereto. Furthermore, bioactive factor loading capacity and bioactive factor discharge capacity may be suitably controlled by regulating a mixing ratio of organic/inorganic components.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The following preferred embodiments of the present invention will be described in detail with reference to the annexed drawings. The present invention may, however, be embodied in different forms and should not be construed as limited to the embodiments set forth herein. The embodiments are provided to those skilled in the art for a better understanding of the present invention.

Figure 1:
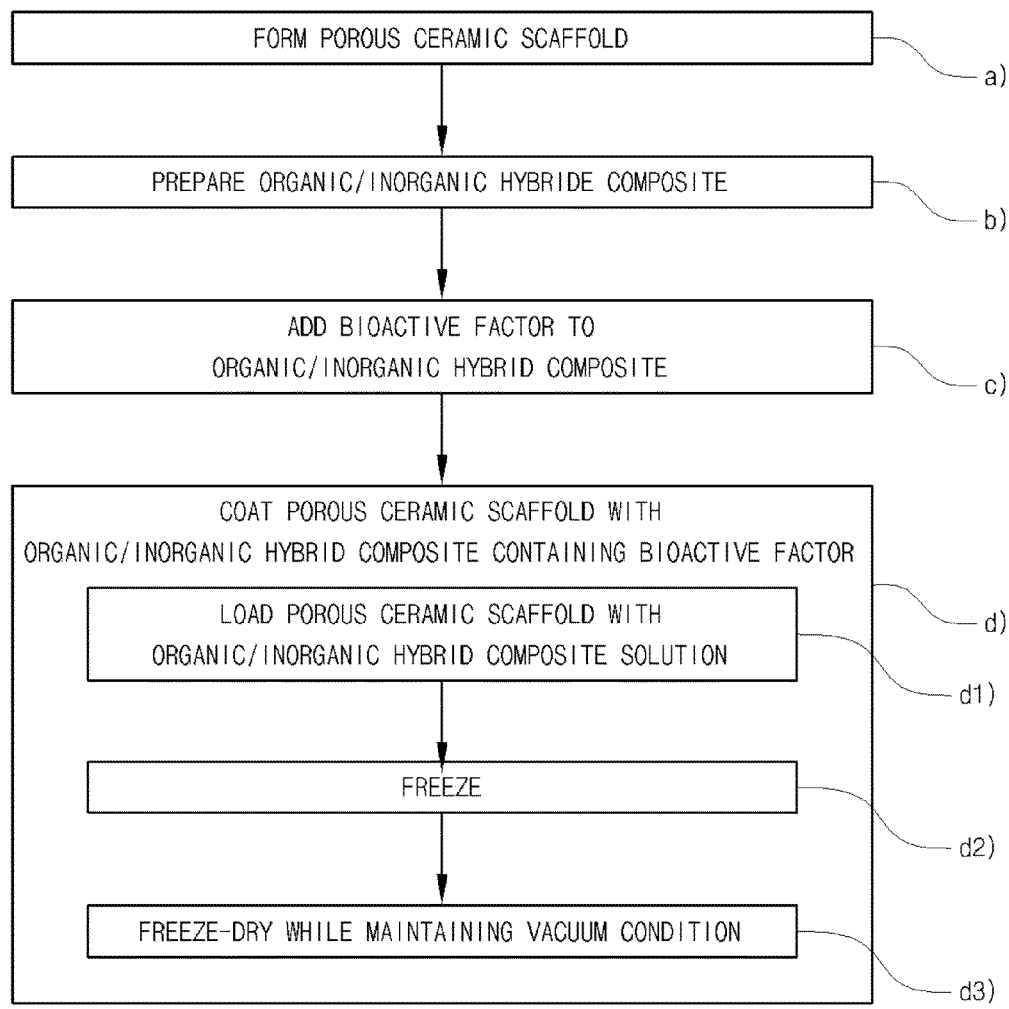
FIG. 1 is a flow chart illustrating a process for manufacturing a porous ceramic scaffold having an organic/inorganic hybrid coating layer containing a bioactive factor, according to the present invention.

As shown in FIG. 1, a method for manufacturing a porous ceramic scaffold having an organic/inorganic hybrid composite coating layer containing a bioactive factor according to the present invention comprises: (a) forming a porous ceramic scaffold; (b) mixing a silica xerogel and a physiologically organic substance to prepare an organic/inorganic hybrid composite; (c) adding a bioactive factor to the organic/inorganic hybrid composite; and (d) coating a pore structure of the porous ceramic scaffold with the organic/inorganic hybrid composite containing the bioactive factor.

Firstly, step (a) is a process of forming and preparing a porous ceramic scaffold and the ceramic material used herein may include, for example, alumina, zirconia, calcium phosphate based materials (hydroxyapatite (HA), tricalcium phosphate (TCP), biphasic calcium phosphate (BCP), etc.), and so forth. More preferably, the porous ceramic scaffold is formed using a calcium phosphate based material having the same elements as components of bones, so as to improve bioactivity. The porous ceramic scaffold may be fabricated through freeze-drying using camphene. Korean Patent No. 879127, entitled "Method for controlling pores of porous material through freeze-casting and porous material manufactured by the same," invented by the present inventors, discloses a process for manufacturing a porous ceramic scaffold through freeze-drying using camphene. As for the porous ceramic scaffold manufactured according to this technique, porosity, pore size, pore arrangement, or the like may be easily controlled depending upon a volume ratio of camphene to ceramic powder, casting time, temperature gradient, etc. That is, since the present invention employs a freeze-drying method using camphene to fabricate a porous ceramic scaffold from a calcium phosphate based ceramic, the fabricated porous ceramic scaffold may have advantages such as easy control of desired pores and improved biocompatibility.

Next, step (b) is a process of forming an organic/inorganic hybrid composite, which includes preparation of an organic/inorganic composite solution by a sol-gel method at room temperature, using a silica xerogel and a physiologically active organic substance. This prepared composite solution is used to further form an organic/inorganic composite solution containing a bioactive factor. The silica xerogel is a vitreous material having pores with a size of several nanometers and is an inorganic material having a silicate ($SiO_2$) structure, which is prepared from a silicon based alkoxide through hydrolysis and condensation. In the case where the silica xerogel is formed by mixing corresponding materials at room temperature and subjecting the mixture to sol-gel processing, side products such as ethanol, methanol, water, hydrochloric acid, etc., may be easily removed through drying and washing and the formation of the silica xerogel may be simply accomplished. In order to control the pore structure of the silica xerogel, a ratio of an alkoxide material to a solvent during hydrolysis, a catalytic material, etc. may be suitably regulated within a range commonly understood by those having ordinary skilled in the art. Such a catalytic material may include an acidic catalyst, without being particularly limited thereto. Korean laid-open Patent Publication No. 10-2009-44858, entitled "Silica xerogal physiologically active organic substance hybrid composites and preparation method thereof" invented by the present inventors, describes the preparation of organic/inorganic hybrid composites through sol-gel processing in detail.

The physiologically active organic substance may include, for example, chitosan, collagen, gelatin, starch, polylactide (PLA), polyglycolide (PGA), poly(lactideglycolide) random copolymer (PLGA), polycaprolactone (PCL), polyethyloxide (PEO), polyethylglycol (PEG), and so forth. Natural polymer may also be used and chitosan is most preferably used.

A physiologically active organic substance solution is added to a silica xerogel (precursor), followed by uniformly mixing to prepare a liquid composite. A constituent ratio of silica xerogel/physiologically active organic substance may be 30~90:70~10 (by volume) and, more preferably, 50~70: 50~30 (by volume). If a content of the silica xerogel is too high, a coating layer of the porous ceramic scaffold, which is formed of the organic/inorganic composite prepared through freeze-drying, shows decreased mechanical properties and morphology of the scaffold may be easily collapsed by water during washing. When a content of the physiologically active organic substance is too high, biocompatibility may be insignificant and an amount of the bioactive factor possibly loaded in the hybrid composite may be limited.

Using the prepared organic/inorganic hybrid composite, a variety of bioactive factors including a drug, growth factors, proteins, hormones, etc., as described below, may be directly loaded during manufacture of the scaffold.

Following this, step (c) comprises adding a bioactive factor to the prepared hybrid composite based on the silica xerogel/physiologically active organic substance.

The present invention is characterized in that all processes are executed at room temperature. Accordingly, the bioactive factor, which exhibits very weak heat resistance, may be loaded in the hybrid composite to thereby form a specific morphology without problems such as modification thereof during processing.

The adding of the bioactive factor to the hybrid composite includes preparing an organic/inorganic hybrid composite solution and, at the same time, loading the bioactive factor therein. In this case, the resulting material is sufficiently agitated till just before gelation, in order to attain a uniform distribution of the bioactive factor in the hybrid composite solution.

As such, since the bioactive factor is directly loaded in the organic/inorganic hybrid composite solution according to the present invention, a large amount of drug may be introduced into a material and an amount of the bioactive factor possibly loaded in the material may be controlled.

Such a bioactive factor may include a drug, e.g., antibacterial and/or anti-inflammatory agents, for example: beta-lactam antibiotics such as penicillin, cephalosporin, etc.; tetracycline antibiotics such as tetracycline, metacycline, minocycline, etc.; aminoglycoside antibiotics such as kanamycin, gentamycin, ribostamycin, tobramycin, neomycin, etc.; lincoside antibiotics such as lincomycin, clindamycin, etc.; other antibiotics such as vancomycin, cephalexin, cefaclor, cefamandole, etc., in addition, antipyretics such as heparin, paclitaxel, dichloropyrane, etc.

The bioactive factor may include, for example, growth factors such as bone morphogenic protein (BMP), fibroblast growth factor (FGF), vascular endothelial growth factor (VEGF), epidermal growth factor (EGF), etc., protein or hormones such as insulin, or the like.

Then, step (d) comprises coating of a pore structure of the prepared ceramic scaffold with the organic/inorganic composite containing the bioactive factor. More particularly, step (d) may include (d1) loading the porous ceramic scaffold with the organic/inorganic hybrid composite solution containing the bioactive factor, (d2) freezing the solution loaded scaffold at a predetermined temperature, and (d3) freeze-drying the scaffold to remove the organic/inorganic hybrid composite solution as a solvent while maintaining a vacuum condition at a predetermined temperature.

In step (d1), by loading the porous ceramic scaffold with the organic/inorganic hybrid composite solution containing the bioactive factor, the organic/inorganic hybrid composite solution containing the bioactive factor may suitably permeate into a pore structure, thus increasing a loading ratio thereof. Moreover, step (d1) may be executed under vacuum. Owing to such vacuum conditions, the organic/inorganic composite solution may be uniformly loaded inside the pore structure of the ceramic scaffold. In addition, in step (d2), a temperature is set to not more than a freezing point of the solvent, enabling the hybrid composite solution to be sufficiently frozen. In order to impart such conditions, the porous ceramic scaffold is subjected to freezing at a temperature of −60° C. or less. Meanwhile, in step (d3), drying is carried out in the same range of temperatures (−60° C. or less) as that in step (d2), under vacuum. As a result, only the solvent is removed while retaining an original morphology of the hybrid composite solution loaded into an internal pore structure. Accordingly, a uniform coating layer may be formed inside the pore structure and, compared to a general coating method performed via dipping, a porous coating layer may be formed through drying under a constant freezing condition.

According to the foregoing processes, the hybrid composite solution may fill the pore structure of the ceramic scaffold, thus forming a coating layer. Consequently, when the pore structure of the ceramic scaffold is coated with the organic/inorganic hybrid composite containing a bioactive factor, a surface area of the ceramic scaffold may be increased, thereby improving biocompatibility and bioactivity.

Figure 2:
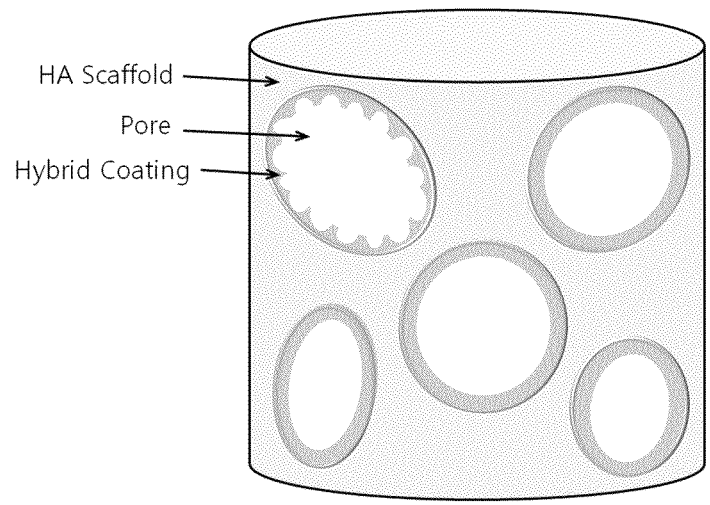
FIG. 2 is a schematic view illustrating a porous ceramic scaffold having an organic/inorganic hybrid coating layer containing a bioactive factor, manufactured according to an exemplary embodiment of the present invention.

The present invention also provides a porous ceramic scaffold having an organic/inorganic hybrid coating layer containing a bioactive factor, formed by the manufacturing method described above. FIG. 2 schematically illustrates a porous ceramic scaffold having an organic/inorganic hybrid coating layer containing a bioactive factor, manufactured according to the present invention. As shown in the figure, the organic/inorganic hybrid coating layer containing the bioactive factor is uniformly formed throughout a surface of the ceramic scaffold having a pore structure (that is, pores).

Hereinafter, the present invention will be explained in greater detail with reference to the following examples. However, these examples are given for the purpose of illustration and are not intended to limit the present invention.

EXAMPLES

Example 1

In Step 1, hydroxyapatite was treated in a solvent comprising camphene, using a ball-mill at 60° C. for 3 to 6 hours. Herein, a content of ceramic may be controlled to 10 to 40 parts by volume. The prepared ceramic slurry was poured into a mold to impart a predetermined morphology thereto, was casted at 44° C. for 3 days. In this regard, casting time may be controlled to 1 to 5 days depending upon desired pore size. The casted green-body was immediately frozen at −70° C. and, after removing the mold, was subjected to drying while maintaining a vacuum condition at −60° C., in order to remove camphene. Thereafter, the freeze-dried hydroxyapatite was sintered at 1300° C. for 3 hours, thus forming a porous ceramic scaffold.

In Step 2, a silica alkoxide, water and hydrochloric acid (1N) as a catalyst were prepared and agitated at 400 to 600 rpm for 1 hour, to synthesize a silica xerogel. Then, a chitosan solution in an amount corresponding to 50% (by volume) of a hybrid composite solution was added to the synthesized silica xerogel.

In Step 3, vancomycin (a bioactive factor) in a calculated concentration of 10 to 30 mg/ml was added to a mixed solution including the silica xerogel and the chitosan solution under agitation, followed by stirring for additional 2 to 3 hours.

In Step 4, after the porous hydroxyapatite scaffold formed in Step 1 was loaded with an organic/inorganic composite solution containing vancomycin, vacuum was maintained for a predetermined time to enable the hybrid composite solution to be loaded into a pore structure of the scaffold. Following this, a carrier formed by loading the organic/inorganic hybrid composite solution into the pore structure of the ceramic scaffold was quenched to −70° C. Finally, the solvent was removed from the organic/inorganic hybrid composite solution while maintaining a vacuum condition at −60° C. for 1 to 2 days, followed by drying and washing.

Example 2

The same procedure as described in Example 1 was executed, except that a quantitative amount of bone morphogenic protein (BMP) was added as a bioactive factor to be loaded in the organic/inorganic hybrid composite, followed by agitation. The amount of the added BMP was 100 μg/ml relative to a total volume of a final organic/inorganic hybrid composite.

Experimental Example

Figure 3A:
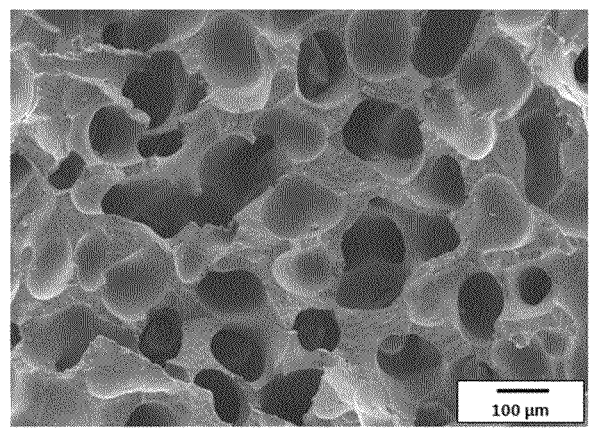
FIG. 3A is a scanning electron microscope (SEM) image showing a surface of a porous hydroxyapatite (HA) formed through freeze-drying using camphene, manufactured in Example 1 of the present invention.
Figure 3B:
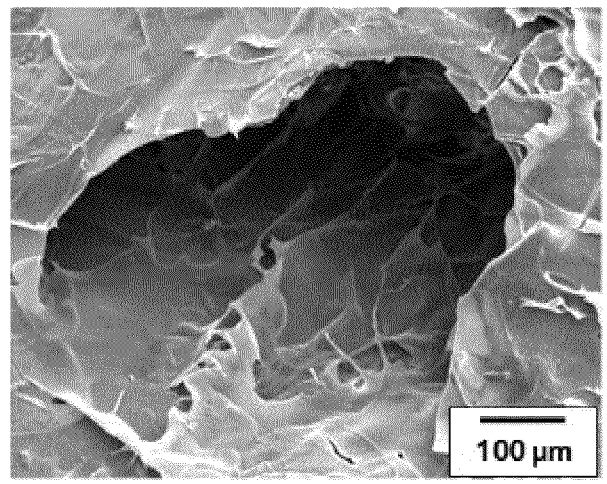
FIG. 3B is an SEM image showing a pore part of a porous ceramic scaffold having a coating layer formed of an organic/inorganic hybrid composite containing a drug, manufactured in Example 1 of the present invention.

Structure of a Porous Ceramic Scaffold having an Organic/Inorganic Hybrid Composite Coating Layer Containing a Bioactive Factor FIG. 3A is a scanning electron microscope (SEM) image that shows a surface of a porous hydroxyapatite (HA) formed through freeze-drying using camphene, which was manufactured in Step 1 of Example 1, and FIG. 3B is an enlarged SEM image that shows a pore part of a porous ceramic scaffold having a coating layer formed of an organic/inorganic hybrid composite containing a bioactive factor (a drug), manufactured in Example 1. As such, it can be seen that the organic/inorganic hybrid substance is uniformly applied throughout a surface of the scaffold having pores.

Figure 4:
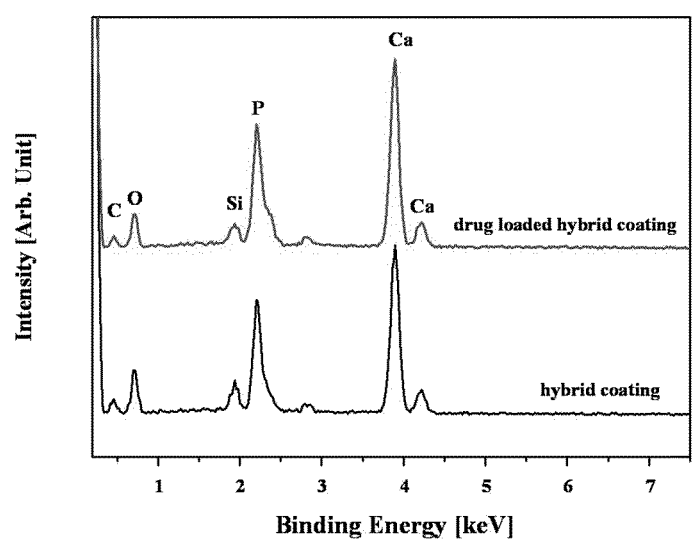
FIG. 4 is graphs showing results of qualitative analysis of elements contained in porous ceramic scaffolds through energy dispersive spectroscopy (EDS), wherein the porous ceramic scaffolds have respective coating layers including an organic/inorganic hybrid composite and an organic/inorganic hybrid composite containing a bioactive factor, respectively, manufactured in Example 1 of the present invention.

Phase Analysis of Porous Ceramic Scaffold having an Organic/Inorganic Hybrid Composite Coating Layer Containing a Bioactive Factor FIG. 4 is graphs showing results of qualitative analysis of elements contained in porous ceramic scaffolds through energy dispersive spectroscopy (EDS), wherein the porous ceramic scaffolds have respective coating layers including an organic/inorganic hybrid composite (lower graph) and an organic/inorganic hybrid composite containing a bioactive factor (upper graph), manufactured in Example 1. From these graphs, other than calcium and phosphate elements which are ingredients of the ceramic scaffold, major elements of an organic/inorganic hybrid composite solution and silica element can be found. Moreover, it can be seen that the hybrid composite is uniformly applied to a surface of the ceramic scaffold regardless of the drug added thereto.

Figure 5A:
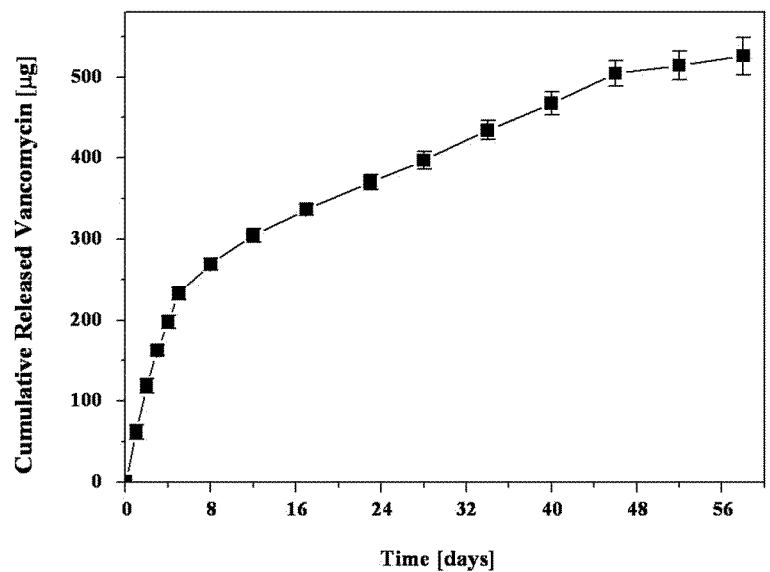
FIG. 5A is a graph showing assessment result of discharge capacity of a porous ceramic scaffold having an organic/inorganic hybrid coating layer that contains vancomycin as an antibiotic, manufactured in Example 1 of the present invention.
Figure 5B:
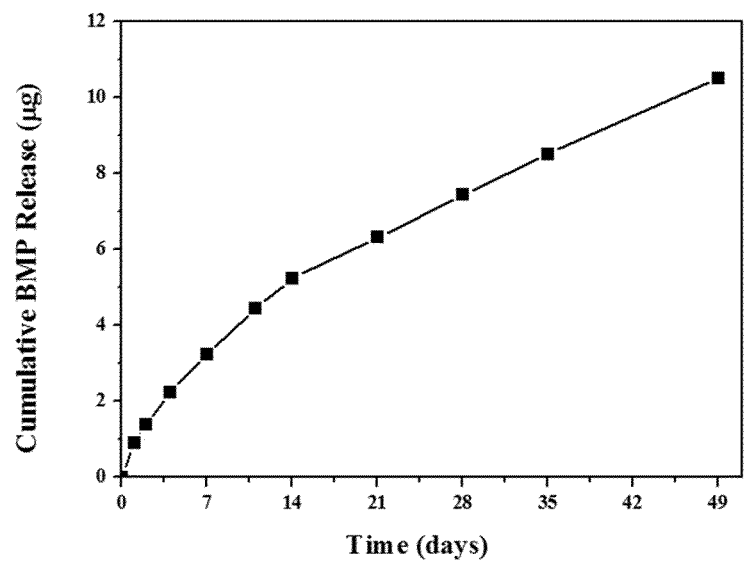
FIG. 5B is a graph showing assessment result of discharge capacity of a porous ceramic scaffold having an organic/inorganic hybrid composite coating layer in which a bone morphogenic protein (BMP) as a growth factor is contained, manufactured in Example 2 of the present invention.

Assessment of Discharge Capacity of Porous Ceramic Scaffold having Coating Layer Based on Organic/Inorganic Hybrid Composite Containing Bioactive Factor FIG. 5A is a graph showing assessment results of discharge capacity of a porous ceramic scaffold having an organic/inorganic hybrid composite coating layer that contains vancomycin as an antibiotic drug, manufactured in Example 1 of the present invention, and FIG. 5B is a graph showing assessment results of discharge capacity of a porous ceramic scaffold having an organic/inorganic hybrid composite coating layer in which bone morphogenic protein (BMP) as a growth factor is contained, manufactured in Example 2 of the present invention. As shown in these figures, it can be seen that the organic/inorganic hybrid composite coating layer may carry and discharge not only a drug such as antibiotics but also a growth factor as a protein species in sufficient amounts. Moreover, it can also be identified that the foregoing coating layer may continuously discharge such bioactive factors in a predetermined amount for a long period of time from 1 to 2 months.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for manufacturing a porous ceramic scaffold having an organic/inorganic hybrid coating layer containing a bioactive factor, comprising:
   (a) forming a porous ceramic scaffold comprised of a ceramic material having pores by freeze-drying using camphene as a freezing medium, the ceramic material being selected from the group consisting of hydroxyapatite (HA), tricalcium phosphate (TCP), biphasic calcium phosphate (BCP), alumina, and zirconia;
   (b) mixing a silica xerogel and a physiologically active organic substance in a volumetric ratio ranging from 30:70 to 90:10 and treating by a sol gel method to prepare an organic/inorganic hybrid composite solution;
   (c) adding a bioactive factor to the organic/inorganic hybrid composite solution and agitating until gelation occurs; and
   (d) coating the porous ceramic scaffold with the organic/inorganic composite containing the bioactive factor added thereto.

2. The method according to claim 1, wherein the physiologically active organic substance is at least one of chitosan, gelatin, collagen, starch, polylactide (PLA), polyglycolide (PGA), poly(lactideglycolide) random copolymer (PLGA), polycaprolactone (PCL), polyethyloxide (PEO), and polyethylglycol (PEG).

3. The method according to claim 1, wherein the bioactive factor is a drug selected from the group consisting of antibacterial agents, anti-inflammatory agents, and antipyretics.

4. The method according to claim 1, wherein the bioactive factor is a growth factor selected from the group consisting of a bone morphogenic protein (BMP), a fibroblast growth factor (FGF), an epidermal growth factor (EGF), a vascular endothelial growth factor (VEGF), a protein, and a hormone.

5. The method according to claim 1, wherein Step (d) includes:
   (d1) loading the porous ceramic scaffold with the organic/inorganic hybrid composite solution containing the bioactive factor;
   (d2) freezing the solution loaded scaffold at a predetermined temperature; and
   (d3) freeze-drying the resulting material to remove the solvent while maintaining a vacuum condition at a predetermined temperature.

6. The method according to claim 5, wherein Step (d1) includes loading the porous ceramic scaffold with the organic/inorganic hybrid composite solution containing the bioactive factor under vacuum.

7. The method according to claim 1, wherein all processes in Steps (b) to (d) are executed at room temperature.

8. The method according to claim 3, wherein the drug is at least one antibacterial agent selected from the group consisting of a beta-lactam antibiotic, a tetracycline antibiotic, an aminoglycoside antibiotic, a lincoside antibiotic, vancomycin, cephalexin, cefaclor, and cefamandole.

9. The method according to claim 8, wherein the beta-lactam antibiotic is penicillin or cephalosporin; the tetracycline antibiotic is tetracycline, metacycline or minocycline; the aminoglycoside antibiotic is kanamycin, gentamycin, ribostamycin, tobramycin or neomycin; and the lincoside antibiotic is lincomycin or clindamycin.

10. The method according to claim 8, wherein the antipyretic is heparin.

11. The method according to claim 4, wherein the hormone is insulin.

12. A method for manufacturing a porous ceramic scaffold having an organic/inorganic hybrid coating layer containing a bioactive factor, comprising:
- (a) forming a porous ceramic scaffold comprised of a ceramic material having pores;
- (b) mixing a silica xerogel and a physiologically active organic substance to prepare an organic/inorganic hybrid composite solution;
- (c) adding a bioactive factor to the organic/inorganic hybrid composite solution; and
- (d) coating the porous ceramic scaffold with the organic/inorganic composite containing the bioactive factor added thereto by:
  - (d1) loading the porous ceramic scaffold with the organic/inorganic hybrid composite solution containing the bioactive factor under vacuum;
  - (d2) freezing the solution loaded scaffold at a predetermined temperature; and
  - (d3) freeze-drying the resulting material to remove the solvent while maintaining a vacuum condition at a predetermined temperature.

* * * * *